(12) United States Patent
Reis

(10) Patent No.: US 7,347,552 B2
(45) Date of Patent: Mar. 25, 2008

(54) DEVICE FOR EXAMINING THE ANTERIOR AND THE POSTERIOR SEGMENTS OF THE EYEBALL

(76) Inventor: Werner Reis, Franz-Fihl-Str. 3d, 80992 Munich (DE)

( * ) Notice: Subject to any disclaimer, the term of this patent is extended or adjusted under 35 U.S.C. 154(b) by 288 days.

(21) Appl. No.: 11/221,804

(22) Filed: Sep. 9, 2005

(65) Prior Publication Data

US 2006/0176447 A1 Aug. 10, 2006

(30) Foreign Application Priority Data

Sep. 10, 2004 (DE) .................. 10 2004 043 766
Jul. 12, 2005 (DE) .................. 10 2005 032 501

(51) Int. Cl.
*A61B 3/14* (2006.01)

(52) U.S. Cl. .................. 351/214; 351/206; 351/212; 606/3

(58) Field of Classification Search ........ 351/205–207, 351/210–212, 214, 221; 606/3, 24, 13
See application file for complete search history.

(56) References Cited

U.S. PATENT DOCUMENTS 5,865,829 A * 2/1999 Kitajima .................. 606/3

FOREIGN PATENT DOCUMENTS

EP 1 389 943 5/2002

* cited by examiner

*Primary Examiner*—Timothy Thompson
(74) *Attorney, Agent, or Firm*—Antonelli, Terry, Stout & Kraus, LLP.

(57) ABSTRACT

The invention is a device for examining the anterior and the posterior segments of the eyeball in a patient's eye, including a stereoscopic microscope system and an oscillating slit lamp disposed downstream of the stereoscopic microscope in the viewing direction in longitudinal direction to two parallel optical beam paths. The invention in the region between the binocular tube objective system and the main objective provides an optical deflection means which does not optically interfere with the stereoscopic beam paths of the stereoscopic microscope and via which an observation beam path and an illumination beam path of an ophthalmoscope can be coupled in in such a manner that the optical observation beam path and the illumination beam path deflected by the optical deflection means each pass through the main objective in viewing direction.

24 Claims, 4 Drawing Sheets

DEVICE FOR EXAMINING THE ANTERIOR AND THE POSTERIOR SEGMENTS OF THE EYEBALL

TECHNICAL BACKGROUND

Figure 1:
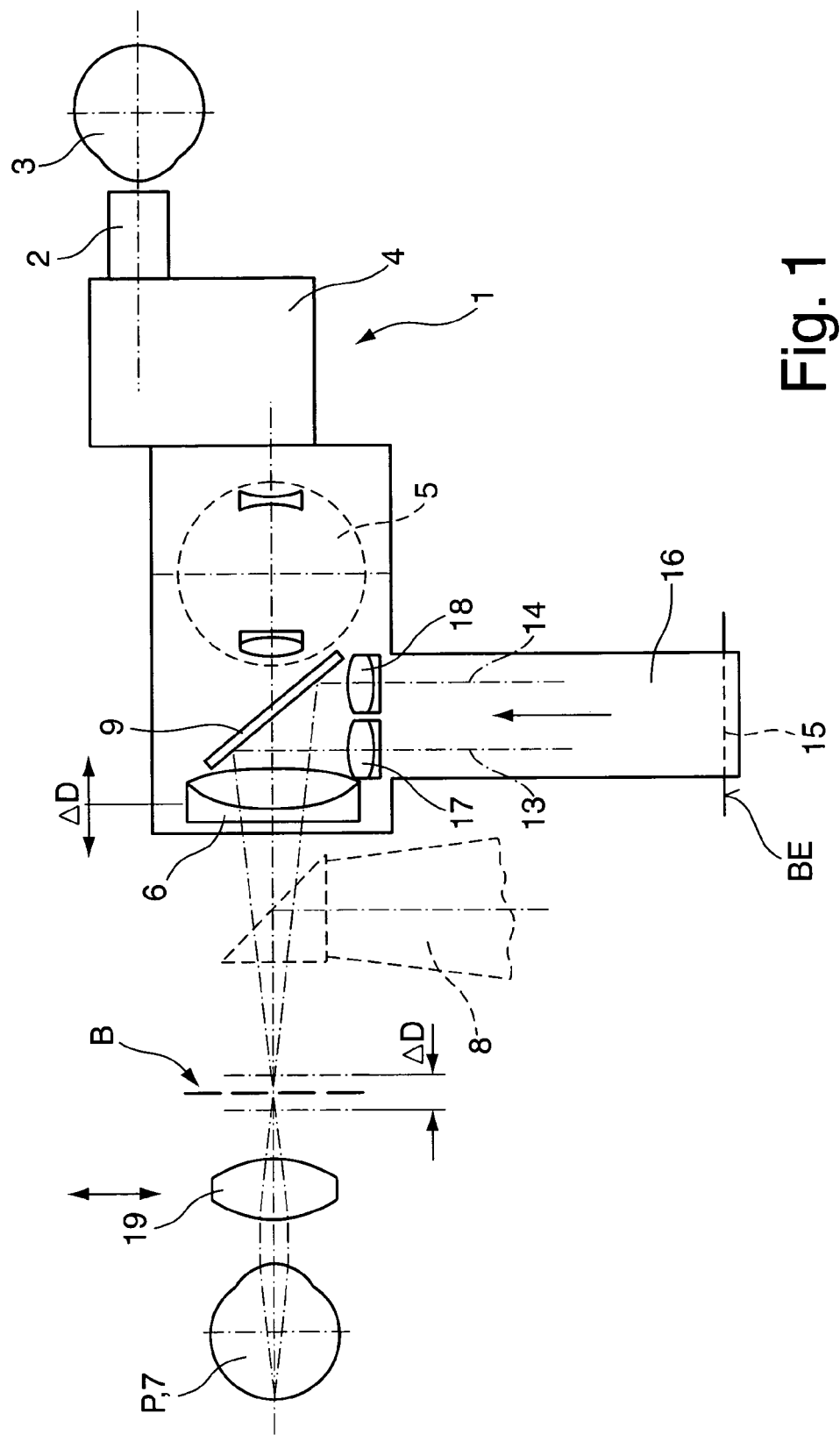

The present invention relates to a device for examining the anterior and the posterior segments of a patient's eye, the device having a stereoscopic microscope system and an oscillating slit illuminator disposed in viewing direction downstream of the stereoscopic microscope in longitudinal direction to two parallel optical beam paths, so-called stereoscopic beam paths, passing through the stereoscopic microscope, in longitudinal direction to whose stereoscopic beam paths, are provided a binocular optic having a downstream binocular tube objective system, an interchangeable Galilean optic and a main objective.

PRIOR ART

Complete ophthalmic diagnosis of a patient's eye demands examining both the anterior and the posterior segments of the eyeball hitherto requiring providing and consecutively using at least two medical diagnostic devices. An as such state-of-the art, slit lamp and a photographic and/or video device for documentation, which can be optionally adjusted to the slit lamp, are employed to examine the anterior segment, i.e. the region of the cornea including the crystalline lens and the near gelatinous vitreous body. Slit lamps usually comprise a stereoscopic microscope, which enables the ophthalmologist to observe the patient's eye magnified by a binocular optic, and an optical imaging system. For selective, preferably streak, illumination of the anterior segment of the eyeball, a slit illuminator is flange-mounted to a stereoscopic microscope system in an oscillating manner. During examination of the anterior segment of the eyeball, the ophthalmologist aligns the slit illuminator laterally to the to-be-examined eye in such a manner that, due to the linear, lateral incidence of light on the interfaces present in the anterior segment of the eyeball, the ophthalmologist sees sickle-shaped light reflection lines matching the surface contour of the interfaces, the light reflection lines, each of which corresponding to a light section line in longitudinal direction to the interfaces illuminated by the slit illuminator in the region of the anterior segment of the eyeball. Although it is basically possible to observe the retina with the aid of such a type slit lamp, thus also the posterior segments, with the aid of additional magnifying lenses or so-called contact lenses, which are placed on the eyeball, the observed beam paths do not permit full overall representation of the retina, respectively of the fundus oculi, due to the observation and the documentation being quite reflection-influenced.

Reliable examination of the posterior segments of the eyeball, in particular the fundus oculi, requires a so-called retina camera, respectively a fundus camera. The optical setup of the fundus camera corresponds to a reflection-free ophthalmoscope, having an intermediate image with which abnormal changes in the fundus oculi, such as detachment of the retina, hemorrhaging of the retina or changes in the blood vessels of the retina, can be diagnosed. A halogen lamp is employed as a light source for observation using a stereoscopic microscope. A flash lamp is used for photographic documentation. Its great light power is needed as the emission of the retina lies in the range of only $10^{-3}$ to $10^{-5}$. The disadvantage of conventional fundus cameras is continuous illumination of the fundus oculi and poor contrast imaging of the fundus oculi due to scattered light. So-called scanning systems which permit illuminating and simultaneously observing only a small region of the fundus oculi by means of slit-shaped oscillating diaphragms in the observation beam path and in the illumination beam path offer distinct advantages with regard to improved image quality. In order to nonetheless be able to examine a larger part of the fundus oculi, the illumination diaphragm and the observation diaphragm are moved synchronously due to which a part of the fundus oculi is scanned. If the fundus oculi is observed with a detector, which has a certain inertia, and if the slit images of the diaphragms move fast enough over the same part of the fundus oculi, the single images fuse to a whole image of the scanned part of the fundus oculi. Such types of scanning ophthalmoscopes permit observing the fundus oculi, particularly in the case of already opaque lenses, by reducing the generation and the observation of scattering light and the resulting glare. In this case, a real intermediate image is generated outside the eyeball in front of the cornea by means of an ophthalmoscope lens, with the illumination device and the magnifying optical system of the ophthalmoscope being focussed on the plane of this intermediate image. An especially preferred designed ophthalmoscope is described in EP 1 389 943 B1.

SUMMARY OF THE INVENTION

The object of the present invention is to reduce the technical complexity of the device and, thus, the costs for an ophthalmologist who needs to diagnose the entire eye, i.e. from the anterior to the posterior segment of the eyeball.

The solution to the object of the present invention is set forth in claim 1. Features which advantageously further develop the inventive idea are the subject matter of the subordinate claims.

The present invention is based on the desire to seek a cost-effective as possible mode of diagnosis of the anterior to the posterior segment of the eyeball by creating a device that combines the function of a slit lamp and the function of an ophthalmoscope. According to the solution, a device for examining the anterior and the posterior segments of a patient's eye, the device being provided with a stereoscopic microscope system and an oscillating slit lamp which is disposed downstream of the stereoscopic microscope in viewing direction in longitudinal direction to two parallel optical beam paths, so-called stereoscopic beam paths, passing through the stereoscopic microscope in longitudinal direction to the stereoscopic beam paths of which a binocular optic having a binocular tube objective system disposed downstream, an interchangeable Galilean optic and a main objective, is further developed in such a manner that, in the region between the binocular tube objective system and the main objective, an optical deflection means is provided which, on the one hand, does not optically interfere with the stereoscopic beam paths of the stereoscopic microscope and via which, on the other hand, an observation beam path and an illumination beam path can be coupled in such a manner that the observation beam path and the illumination beam path deflected by the optical deflection means each pass through the main objective in viewing direction.

As the region of the stereoscopic beam paths located inside the stereoscopic microscope system between the main objective and the tube objective are each formed as parallel beam paths, this region offers the possibility of integrating additional optical elements without interfering with the stereoscopic beam paths inside the stereoscopic microscope. In order to rule out possible negative effects in longitudinal direction to the stereoscopic beam paths, an optical deflection means, preferably constructed as a mirror or prism system is placed inside the stereoscopic microscope system in such a manner that the deflection means neither cuts nor passes through the stereoscopic beam paths, but rather the aim is to design and place the optical deflection means in such a manner that it is disposed at a lateral distance from the stereoscopic beam paths inside the stereomicroscope system.

In the same manner as in combining a slit lamp system with an ophthalmoscope in a single casing as described in the preceding, a surgical-microscope-type stereoscopic microscope system can be combined with an ophthalmoscope, with in this case the observation beam path and the illumination beam path of the ophthalmoscope being coupled in via an optical deflection means integrated inside the stereoscopic microscope system in such a manner that the observation beam path and illumination beam path deflected by the optical deflection means each pass through the main objective of the surgical microscope system in viewing direction. By means of this measure, a normal surgical microscope built as a stereoscopic microscope is further developed with the properties of an ophthalmoscope, thereby opening the additional possibility of examining posterior segments of the eyeball with a surgical microscope system.

Regardless whether it is the proposed combination of a slit lamp and an ophthalmoscope or a combination of a surgical microscope and an ophthalmoscope, coupling in the ophthalmoscope-side illumination beam and the observation beam requires two spatially separate deflection regions on the optical deflection unit in order to deflect the two beam paths in parallel inside the stereoscopic microscope system to the stereoscopic beam paths which all pass through the main objective of the stereoscopic microscope system together in viewing direction.

As, due to suited construction and arrangement of the optical deflection means, the beam paths of both the stereoscopic microscope system and the ophthalmoscope do not interfere with each other, it is much easier for the ophthalmologist to conduct a full examination of a patient's eye. If first the anterior segment of the eyeball is to be examined, the ophthalmologist employs the stereoscopic microscope system in the usual manner by observing through the binocular optic of the microscope system. If then regions of the posterior segment of the eyeball are to be diagnosed, the lighting of the stereoscopic microscope only needs to be switched off and the ophthalmoscope part of the device built according to the solution needs to be activated in that a light source provided in longitudinal direction to the illumination beam path is switched on. In order to image the fundus oculi in an intermediate image plane that lies outside the eye, in addition an ophthalmoscope lens has to be positioned opposite the to-be-examined eye. The ophthalmoscope lens is preferably integrated in a module which can be mounted firmly, but detachable, to a reception structure provided in the region of the main objective of the stereoscopic microscope system.

The observation beam path and the illumination beam path pass through the ophthalmoscope lens, the illumination beam path being imaged on the posterior segment of the eyeball, i.e. on the retina, and the retina being imaged in longitudinal direction to the observation beam path through the ophthalmoscope lens in the intermediate image plane which is conveyed with the aid of the main objective of the stereoscopic microscope into a parallel beam which then is imaged in longitudinal direction to suited imaging optics preferably onto a camera unit located in the image plane of the ophthalmoscope.

The optical components of the stereoscopic microscope system and the optical components allocatable to the ophthalmoscope are preferably located in a single compact, user-friendly casing. With the aid of such a type device built according to the solution, the treating ophthalmologist is able to examine the anterior and the posterior segments of a patient's eye at a single workplace without placing the patient, as previously customary, before two different instruments. The yielded time gain and the capability of uninterrupted documentation of eye diagnosis in the anterior segment as well as in the posterior segment of the eyeball results in distinctly reducing the time and cost required for the eye examination. The optical unit module allocated to the ophthalmoscope can, of course, also be firmly, but detachably, mounted on the casing of the stereoscopic microscope via a corresponding mechanical interface.

Further details of the device according to the solution which combines the function of a slit lamp and the function of an ophthalmoscope, preferably a scanning ophthalmoscope, in a single device are found in the subsequent description with reference to the description of concrete preferred embodiments.

Here, a particular expansion according to the present solution of the functionality of an ophthalmoscope as preferably drawn from EP 1 389 943 B1 is pointed out. In a similar manner, in which in the preceding, by providing a coupling-in mirror in longitudinal direction to the beam path of the stereoscopic microscope system, the functionality of the stereoscopic microscope is expanded with the added functionality of an ophthalmoscope, it is similarly possible with the ophthalmoscope described in EP 1 389 943, which is particularly distinguished by an ophthalmoscope section in longitudinal direction to which the observation beam and the illumination beam are formed as parallel beams running parallel to each other to couple in the image of a display surface, by integrating in the ophthalmoscope an optical deflection mirror in longitudinal direction to the aforedescribed parallel-beam path, which permits microperimetric examination of the patient's eye.

Based on an ophthalmoscope described in EP 1389 943 B1 for examining a patient's fundus oculi, the ophthalmoscope having the features of the generic part of claim 19, the innovation is distinguished by providing in the region of the infinitely imaged intermediate image plane, i.e. in the region of the observation beam paths and the illumination beam paths running as parallel beams inside the ophthalmoscope, an optical deflection element, preferably in the form of a mirror or a deflection prism via which an additional beam path can be coupled in longitudinal direction to the illumination and/or the observation beam. Furthermore, the additional beam path is formed as a projection beam path in longitudinal direction of which an objective is placed in whose focal point a display, preferably a LCD display, is placed which is infinitely imaged by the objective while forming a parallel beam path which can be coupled in longitudinal direction to the illumination beam and the observation beam by the optical element.

In an advantageous manner, a self-illuminating LCD display, for example having 1024×768 separately activatable pixels, is infinitely imaged via an objective. Via the optical deflection element located in the telecentric beam path of the ophthalmoscope, the display is imaged via an optical unit inside the ophthalmoscope in the intermediate plane of the ophthalmoscope lens. This ophthalmoscope lens, which usually is placed opposite the to-be-examined patent's eye, images the image of the display at the site of the retina of the patient's to-be-examined eye. The intrinsic ophthalmic optical unit in the form of an objective, by means of which the observation beam path and the illumination beam path are both similarly imaged in the intermediate image plane, is designed axially adjustable in longitudinal direction to the parallel beam path and thus serves to compensate for the aberrations of the patient's to-be-examined eye so that the patient's eye can see the display sharply.

The novel combination of an as such state-of-the-art ophthalmoscope according to the aforecited European printed publication EP 1 389 943 B1 and an image of an LCD display coupled into the ophthalmoscope beam path permits conducting microperimetric examinations on the eyeball in the following manner. Provided in the illumination beam path of the ophthalmoscope is a pivotable infrared filter which prevents the glare of the illumination light on the eye when swung into the illumination beam path. Simultaneous to pivoting in the filter into the illumination beam path, the image of the display is superimposed on the image of the fundus oculi obtained within the scope of the observation beam path in the image plane of the observation beam path on a screen or on an observation camera, enlargement of the display being adapted to the fundus oculi image. Furthermore, the patient's eye is provided via the display an optical fixation point on which the eye should fix. With suited software, defined pixels of the display acting as stimuli points for the eye can be activated. When a stimulus is seen, it is confirmed by the patient with the aid of a suited device, for example by means of a key device, and the position is registered on the screen, respectively on an observation camera. With this method, defect regions on the fundus oculi can be examined perimetrically. Using an as such state-of-the-art eye-tracking method, the image of the display in the image plane of the ophthalmoscope, in which the observation camera is provided, can be superimposed exactly pixel for pixel on the image of the patient's fundus oculi in such a manner that it permits pixel-exact positioning of a stimulus on a predefined point on the fundus oculi. In this manner, the stimuli positions can be tracked under real-time conditions permitting locating, registering and documenting very precisely defect regions in the fundus oculi. Further details of this novel combination of an as such state-of-the-art ophthalmoscope, as described in the preceding, and a further developed projection beam path via which a display image can be coupled in by superimposition on the fundus oculi permits previously not possible selectivity in diagnosis and determination of tiny defect regions in the fundus oculi. Further details can be found in the description with reference to the corresponding preferred embodiment.

BRIEF DESCRIPTION OF THE INVENTION

The present invention is made more apparent in the following, without the intention of limiting the scope or spirit of the overall inventive idea, using preferred embodiments with reference to the accompanying drawings.

Figure 2:
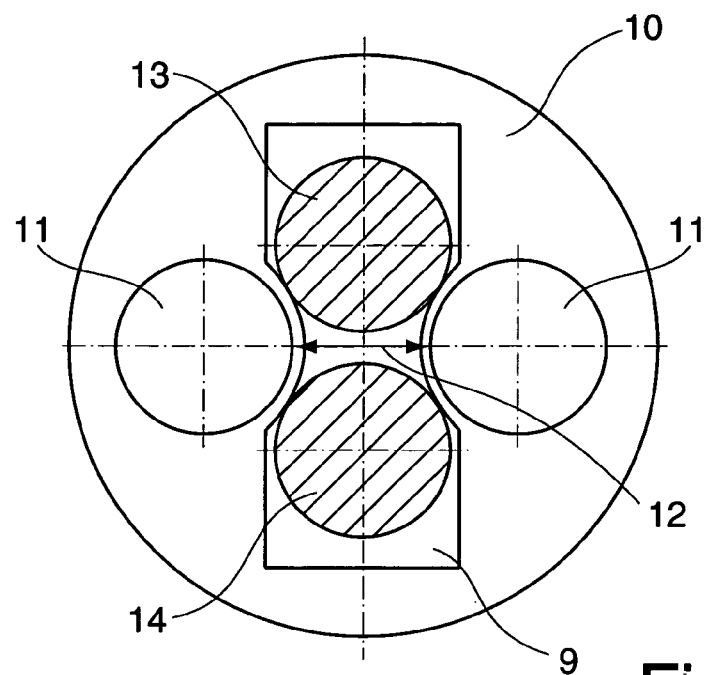
Figure 3:
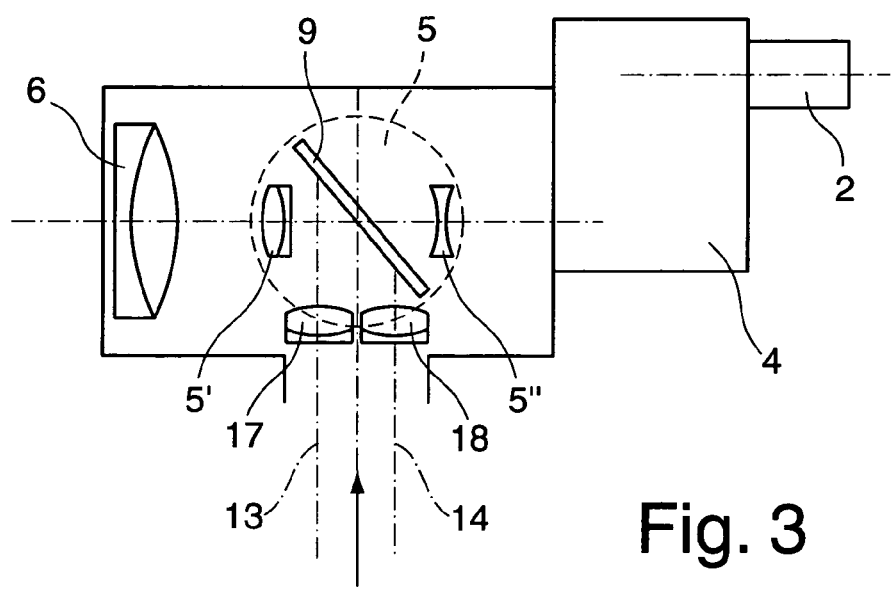
Figure 4:
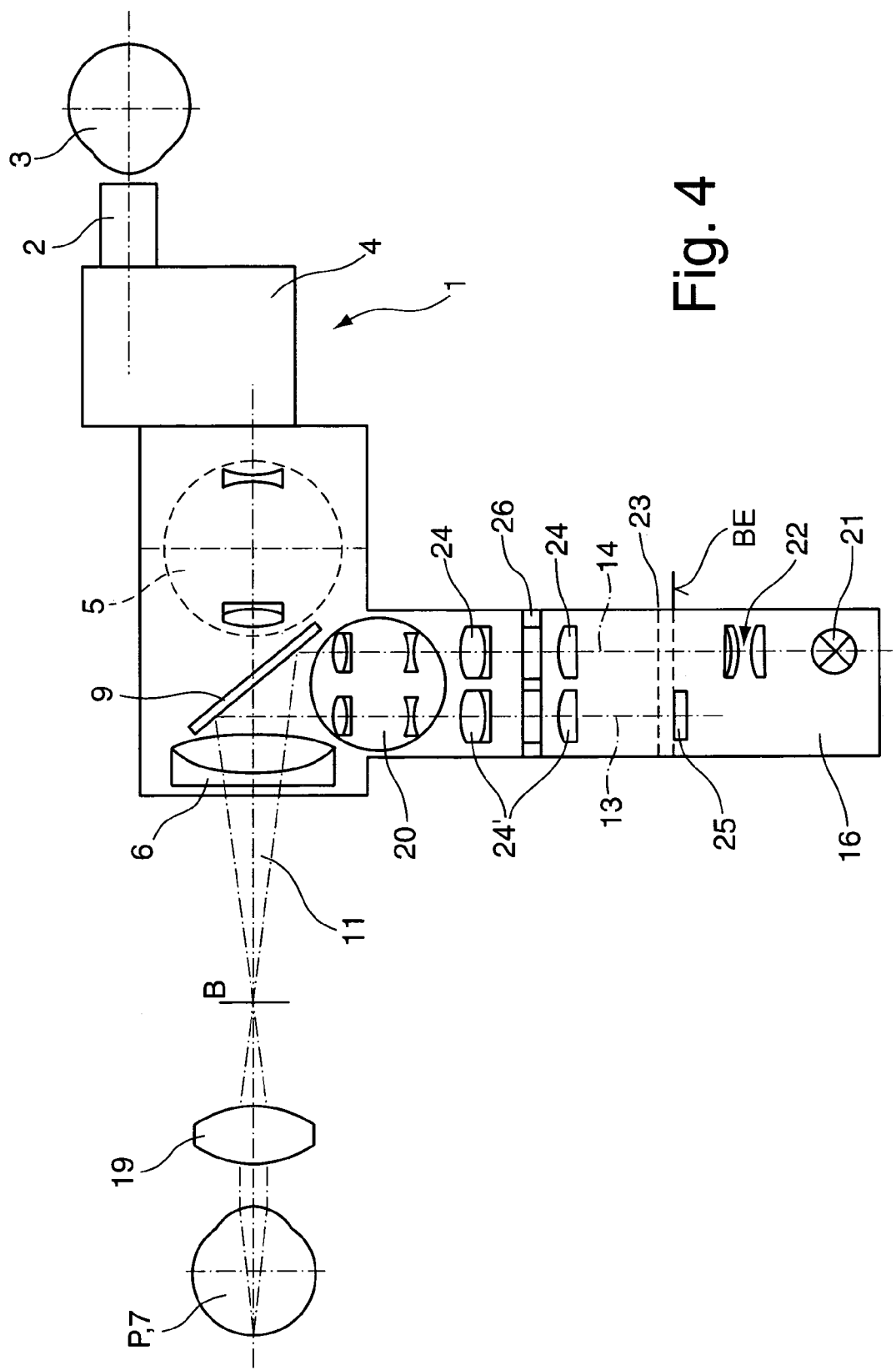
Figure 5:
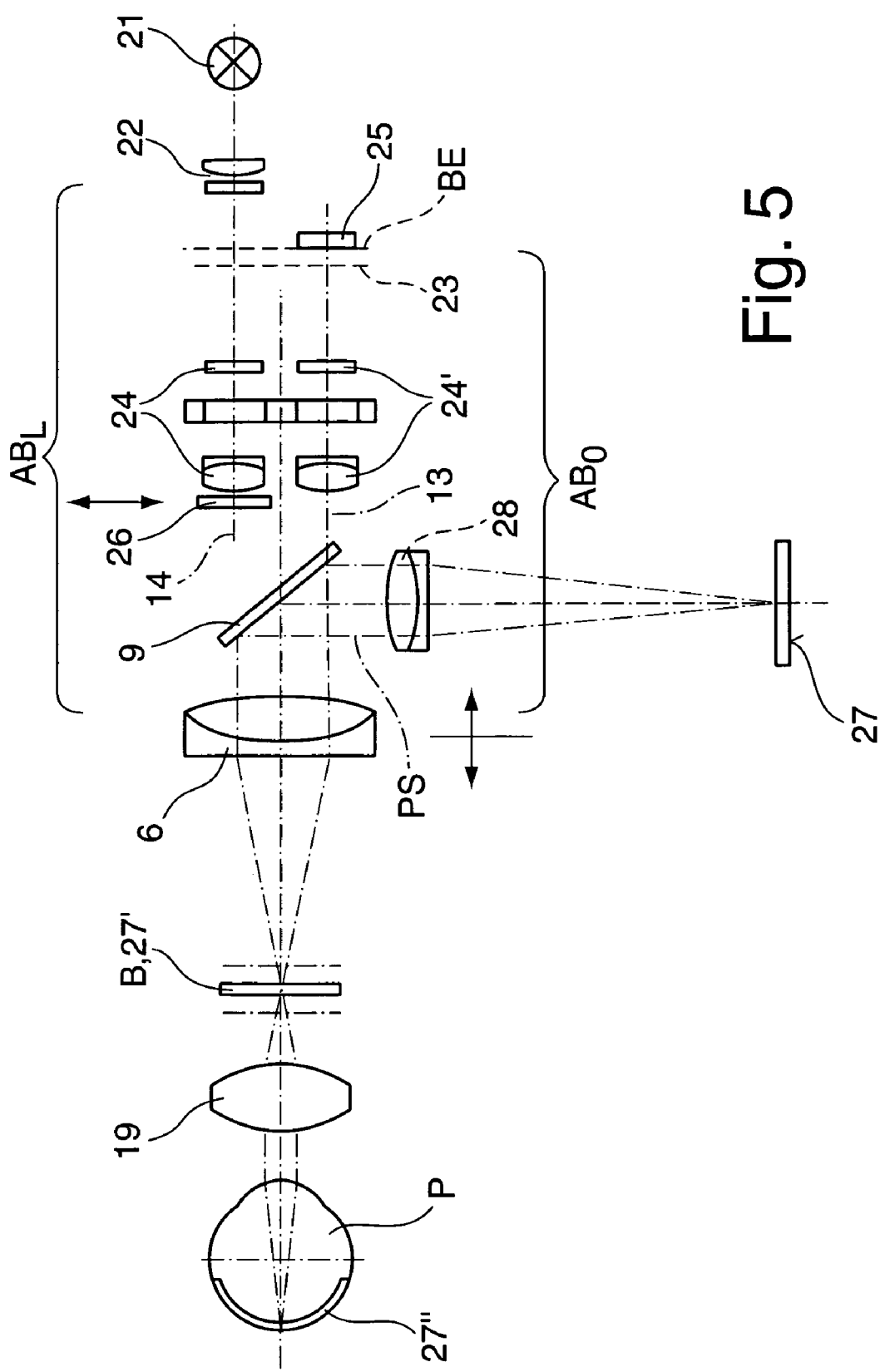

FIG. 1 shows a schematic principle representation of a further developed stereoscopic microscope system according to the present solution, having the observation beam path and the illumination beam path of an ophthalmoscope, FIG. 2 shows a representation of an optical deflection means, FIG. 3 shows a representation of an alternative possible arrangement of the optical deflection means inside the stereoscopic microscope system, FIG. 4 shows a representation of all the optical components of a device built according to the present solution, and FIG. 5 shows a schematic partial representation of an ophthalmoscope with fading in a projection beam path to conduct microperimetric examinations.

WAYS TO CARRY OUT THE INVENTION, COMMERCIAL APPLICABILITY

FIG. 1 shows a schematic overview of a device principle with which it is possible to examine the anterior segment as well as the posterior segment of the eyeball. The device comprises a stereoscopic microscope system 1 having a binocular optic 2 through which the examining ophthalmologist's eye 3 views. Provided downstream in the beam path of the binocular optic 2 is a binocular telescope 4 which images the beam path in a parallel beam respectively. For the sake of candor, it is pointed out that the device depicted in FIG. 1 is a lateral sectional representation in such a manner that only one beam path through the stereoscopic microscope system 1 is depicted. The beam paths allocated to the left eye and to the right eye of the ophthalmologist lie parallel to each other in such a manner that in the following they are referred to as stereoscopic beam paths.

Downstream following the binocular telescope 4 is an interchangeable Galilean optic 5 with which the image can be enlarged or reduced. The interchangeable Galilean optic 5 is basically composed of a negative and a positive optically effective element which image a parallel beam path in a correspondingly enlarged or reduced parallel beam path. Furthermore, the stereoscopic microscope system 1 provides a main objective 6 which is placed in a moveable manner axially to the viewing direction (see arrow) about a region ΔD to compensate for the aberrations of the patient's to-be-examined eye 7.

Usually the aforedescribed stereoscopic microscope system 1 is combined with slit illuminator 8 disposed downstream of the main objective 6 in viewing direction is a so-called slit lamp. In this case the slit illuminator 8 is attached in a pivotable manner about the stereoscopic microscope system 1.

In the further development according to the present solution of the aforescribed stereoscopic microscope system 1, an optical deflection means 9 is provided in the region between the main objective 6 and the interchangeable Galilean optic 5. The optical deflection means 9 is integrated in the stereoscopic microscope system 1 in such a manner that it does not interfere with the stereoscopic beam paths. In an advantageous manner, the deflection means 9 is designed as a deflection mirror. An especially preferred embodiment is depicted in FIG. 2.

FIG. 2 shows a cross section of the stereoscopic microscope system at the site of the deflection mirror 9. It may be assumed that the casing 10 of the stereoscopic microscope system 1 encloses in a cylindrical manner the optical components lying inside. In the sectional representation of FIG. 2, the visible stereoscopic beam paths 11 are the ones disposed running parallel to each other. The two stereoscopic beam paths 11 are placed a distance 12 apart. Provided between the two stereoscopic beam paths 11 is the optical deflection means 9 in the form of a deflection mirror and constructed and placed in such a manner that the deflection mirror 9 is placed laterally at a distance from the two stereoscopic beam paths 11, thereby completely ruling out interference of the stereoscopic beam paths 11 by the deflection mirror 9.

As is described in the following with reference to the preferred embodiment according to FIG. 1, the deflection mirror 9 permits optically coupling in two further beam paths of an ophthalmoscope 16 which is coupled to the stereoscopic microscope arrangement 1, namely coupling in an observation beam 13 and an illumination beam 14. The observation beam 13 and the illumination beam 14 impinging on the deflection mirror 9 from the ophthalmoscope side are deflected aligned parallel to the stereoscopic beam paths 11 in the viewing direction of the stereoscopic microscope system 1 in such a manner that the stereoscopic beam paths 11 and the illumination and observation beams 13, 14 pass through the main objective 6 of the stereoscopic microscope system 1 in viewing direction together. FIG. 1 schematically shows the coupling of an ophthalmoscope 16 and the optical elements contained therein combined in the representation by the beam-guiding optics 17, 18. The distinguishing feature according to the present solution of the device schematically shown in FIG. 1 is to combine an ophthalmoscope 16 for examining the posterior segment of a patient's eye 7 with a stereoscopic microscope system 1. In an especially advantageous manner the ophthalmoscope 16 and the stereoscopic microscope system 1 are enclosed in a casing which is constructed according to ergonometric principles as well as according to user friendliness and functionality. Alternatively, it is also feasible to construct the ophthalmoscope 16 as a module and to flange-mount it to the stereoscopic microscope system 1 via a coupling structure provided on the casing of the stereoscopic microscope system. In this embodiment form, too, the device has a uniform exterior and can be utilized on the patient at a single examination site.

For examining the posterior section of patient P's eye, the slit illuminator 8 is swung away out of the beam path of the stereoscopic microscope system and in its stead a module having an ophthalmoscope lens 19 is connected with the casing of the stereoscopic microscope system in the region of the main objective 6, for example via a plug connection or a similar detachable connection, such as a bayonet connection. The ophthalmoscope lens 19 is able to image the fundus oculi in an intermediate image plane B from which the intermediate image is imaged via the main objective 6 and the subsequent observation beam 13 inside the ophthalmoscope on an image plane BE in which an observation camera 15, for example in the form of a CCD camera, is disposed to record the fundus image, respectively the image of the fundus oculi, photographically or video technically.

FIG. 3 shows a detail of a stereoscopic microscope system further developed according to the present solution. The detail depicts an alternative arrangement of the optical deflection means 9 inside the stereoscopic microscope system. In the case shown in FIG. 3, the optical deflection means 9 is located as a fixed mirror between the optical components 5' and 5", forming the interchangeable Galilean optic 5. In a corresponding manner, the illumination beam path 13 and observation beam path 14 are aligned relative to the optical deflection means 9. For other already introduced and described references see the preceding figures.

FIG. 4 shows a further developed schematic lateral view of the combination device built according to the present solution. To avoid repetition, for already introduced and described reference see the aforedescribed preferred embodiments. In contrast to the schematically drawn ophthalmoscope 16 of FIG. 1, the preferred embodiment according to FIG. 4 provides in the beam path of the observation beam path 13 and of the illumination beam path 14 in the beam direction before coupling in longitudinal direction to the stereoscopic beam paths 11, i.e. before the optical deflection means 9, an interchangeable Galilean optic 20, with which an enlarged, respectively a reduced image of the observation beam path 13 and the illumination beam path 14 of the ophthalmoscope 16 is possible. Furthermore, FIG. 4 shows all the optical components required for the manner of functioning of the ophthalmoscope. The illumination means 21, which provides a halogen lamp as the light source, is followed by an imaging optic composed of a multiplicity of optical components which is allocated to the illumination beam 14. In detail the imaging optic comprises a condenser optic 22, which images the light of the halogen lamp 21 in a homogeneously lit area in the imaging plane BE, in which the slit diaphragm system 23, which oscillates in relation to the illumination beam 14, is provided. An optic unit 24 in the form of a multi-lens objective which conveys the illumination beam 14 into a parallel beam is provided following the slit diaphragm system 23 in beam direction. Finally, as previously mentioned an interchangeable Galilean optic 20 which images enlarged or reduced the illumination beam 14 but also the observation beam 13, however the nature of the parallel beam remains unchanged. Via the optical deflection means 9, the observation beam 14 passes through the main object lens 6, which is provided with at least one achromat, with the parallel illumination beam bundle 14 being focused into an intermediate image plane B from which the illumination beam is imaged via an optical imaging unit, the so-called ophthalmoscope lens 19, on the fundus oculi of the patient P's eye.

The light coming from the illumination beam 14 is reflected at the fundus oculi of patient P's eye 7 and is focused in opposite beam direction via the ophthalmoscope lens 19 back into the intermediate image plane B from where the light is imaged via the imaging optic, composed of a multiplicity of optical components and allocated to the observation beam path 13 of the ophthalmoscope 16, in the following manner on an observation means 25 in the form of a CCD sensor.

Starting from the intermediate image plane B, into which the observation beam 13 coming from the fundus oculi of patient P's eye is focused, the observation beam 13 passes through the main objective 6, simultaneously also acting as an imaging medium for the illumination beam 14, and which conveys the observation beam path 13 into a parallel beam bundle. Thus the main objective 6 of the stereoscopic microscope system serves to infinitely image the intermediate image plane B. Provided following the observation beam 13 is an optical unit 24' which is built as a multi-lens objective and serves to image the observation beam 13 directly in the imaging plane BE in which the light-sensitive detector area of the observation means 25 is located. Provided in the observation beam 13 between the optical unit 24' and the observation means 25 is also a slit of the slit diaphragm system 23, which like the slit diaphragm oscillates in the illumination beam 14. Preferably the diaphragm system 23 is realized as a pair of diaphragms which oscillates synchronously inside the illumination beam path and in the observation beam path of the ophthalmoscope. Further details of the ophthalmoscope of the aforedescribed embodiment are found in EP 1 389 943.

Use of a filter 26 in longitudinal direction to the illumination beam 14 inside the ophthalmoscope 16 prevents glare caused by the halogen lamp 21, permitting conducting examination of the fundus oculi in the form of a non-mydriatic mode of proceeding, i.e without using medication to widen the pupil as use of infrared-sensitive detector systems 25 permits corresponding imaging of the fundus oculi of patient P's eye in the infrared wavelength range.

FIG. 5 depicts an ophthalmic system the details of which are described in EP 1 389 943 B1, but is supplemented by an optical coupling-in device with which a projection beam path PS can be superimposed on the observation beam 13 and the illumination beam 14. In detail FIG. 5 shows the following:

An illumination means 21, which provides a halogen lamp as the light source is followed by an imaging optic $A_{Bl}$ composed of a multiplicity of optical components which is allocated to the illumination beam 14. In detail the imaging optic $A_{Bl}$ comprises a condenser optic 22 which images the light of the halogen lamp 21 in a homogeneously lit area in the imaging plane BE in which a slit diaphragm system 23 is provided which oscillates in relation to the illumination beam 14. Following the diaphragm system 23 in beam direction, an optical unit 24, in the form of a multi-lens objective which conveys the illumination beam 14 into a parallel beam. The parallel illumination bundle is focused in an intermediate image plane B via an optical unit 6, which is provided with at least one achromat. The illumination beam is focused from the intermediate image plane B via an optical image unit 19, the so-called ophthalmoscope lens, on the fundus oculi of patient P's eye.

The light coming from the illumination beam is reflected at the fundus oculi and focused in reverse beam direction to the illumination beam path and via the ophthalmoscope lens 19 back into the intermediate image plane B, from where the light is imaged via imaging optic $A_{Bo}$, which is composed of a multiplicity of optical components and is allocated to the observation beam 13 of the ophthalmoscope, in the following manner on the observation means 25 in the form of a CCD sensor.

Starting from the intermediate image plane B, in which the observation beam 13 coming from the fundus oculi is focused, the observation beam 13 reaches the optical unit, preferably in the form of an objective system 6 which simultaneously also acts as imaging medium for the illumination beam 14 and conveys the observation beam 13 into a parallel beam bundle. Thus the optical unit 6 serves to infinitely image the intermediate plane B. Provided following in the observation beam path is an optical unit 24' which is built as a multi-lens objective and serves to directly image the observation beam 13 in the imaging plane BE, in which the light-sensitive detector area of the observation means 25 is located. Also provided in the observation beam between the optical unit 24' and the observation means 25, is a slit of the slit diaphragm system 23, which like the slit diaphragm of the illumination beam path 14 oscillates. The diaphragm system 23 is preferably realized as a pair of slit diaphragms which synchronously oscillate inside the illumination beam path and the observation beam path.

In addition, an optical deflection means 9, preferably as a deflection mirror, at which a projection beam PS is deflected in direction of the observation beam 13 and illumination beam 14 by the optical unit 6, is provided in the region of the parallel guided beam paths with regard to the illumination beam 14 and observation beam 13. The projection beam PS images the surface of a display 27 via an objective system 28 in a telecentric beam bundle, which is then coupled via the optical deflection means 9 in the aforedescribed manner into the beam path of the ophthalmoscope. The image 27' of display 27 is projected via the main objective 6 into the intermediate image plane B and from there via the ophthalmoscope lens 19 onto the fundus oculi of the patient's eye 7, see reference 27". Fading in the display surface permits conducting micrometric examinations on patient P's eye and simultaneously observing the fundus oculi with the aid of the detector unit 25. In addition, a pivotable filter 26 for infrared illumination is provided inside the illumination beam 14 of the ophthalmoscope in such a manner that the patient is not blinded by the glare of the halogen lamp 21. Simultaneously, the display 27 is superimposed on the fundus oculi image on the examining screen 25. With corresponding setting of the objective 28, the display size is selected in such a manner that it can be superimposed the same size as the fundus oculi image on the examining screen. Via the display the patient's eye is provided an optical fixation point and with suited software, defined pixels from the LCD display 27 are activated which act as stimuli for the patient's eye. If the patient sees the stimulus, he confirms the occurrence via a corresponding device, for example with the aid of a pressing device; and the occurrence is registered on an observation monitor 25. With the aid of this method, the defined defects in the fundus oculi of the patient's eye can be perimetrically determined. With the aid of an eye-tracking system operating in real time, the stimuli positions can be tracked corresponding to the fundus oculi image in such a manner that defect areas can be found on the fundus oculi, displayed and documented with great precision.

LIST OF REFERENCE NUMBERS 1 stereoscopic microscope system
2 binocular optic
3 examiner
4 binocular telescope
5 Interchangeable Galilean optic
6 main objective
7 patient's eye
8 split lamp
9 optical deflection means
10 casing of the stereoscopic microscope system
11 stereoscopic beam paths
12 lateral distance
13 observation beam
14 illumination beam
15 observation camera
16 ophthalmoscope
17, 18 optical unit
19 ophthalmoscope lens
20 Galilean alternating optic
21 light source
22 condenser optic
23 split diaphragm system
24 optical unit
24' optical unit
25 examination monitor, CCD sensor, observation means
26 filter
27 display
27' image of the display
27" image of the display on the retina
28 objective unit

What is claimed is:

1. A device for examining the anterior and the posterior segments of the eyeball in a patient's eye, said device having a stereoscopic microscope system and an oscillating slit lamp disposed downstream of the stereoscopic microscope in the viewing direction in longitudinal direction to two parallel optical beam paths, so-called stereoscopic beam paths passing through the stereoscopic microscope, with a binocular optic having a downstream binocular tube object system, an interchangeable Galilean optic as well as a main objective being provided in longitudinal direction to the stereoscopic beam paths, wherein, in the region between the binocular tube objective system and the main objective, an optical deflection means is provided which does not optically interfere with the stereoscopic beam paths of the stereoscopic microscope and via which an observation beam path and an illumination beam path of an ophthalmoscope can be coupled in in such a manner that the optical observation beam path and the illumination beam path deflected by the optical deflection means each pass through the main objective in viewing direction.

2. A device for examining the anterior and the posterior segments of the eyeball in a patient's eye, the device having a surgical-microscope-type stereoscopic microscope system provided with two optical parallel beam paths, so-called stereoscopic beam paths, in the longitudinal direction of which a binocular optic having a downstream binocular tube objective system, an interchangeable Galilean optic as well as a main objective are provided, wherein, in the region between the binocular tube objective system and the main objective, an optical deflection means is provided which does not optically interfere with the stereoscopic beam paths of the stereoscopic microscope and via which an observation beam path and an illumination beam path of an ophthalmoscope can be coupled in in such a manner that the observation beam path and the illumination beam path deflected by the optical deflection means each pass through the main objective in viewing direction.

3. The device according to claim 1, wherein the optical deflection means is a mirror system or prism system.

4. The device according to claim 1, wherein the optical deflection means is placed at a lateral distance from the stereoscopic beam paths.

5. The device according to claim 1, wherein coupling in the observation beam path and the illumination beam path occurs from a half-plane intersecting, preferably in perpendicular direction, the plane spaned by the stereoscopic beam paths.

6. The device according to claim 1, wherein the optical deflection means is placed stationary between two optical components of the interchangeable Galilean optic.

7. The device according to claim 1, wherein the ophthalmoscope is a scanning ophthalmoscope.

8. The device according to claim 1, wherein the ophthalmoscope and the stereoscopic microscope system are housed in the same casing.

9. The device according to claim 1, wherein the ophthalmoscope can be flange-mounted as a module to the casing of the stereoscopic microscope via a mechanical interlace.

10. The device according to claim 1, wherein in viewing direction downstream of the main objective, a reception structure is provided to which a module having an opthalmoscopic lens can be adapted in such a manner that the observation beam path and the illumination beam path pass through the ophthalmoscope lens.

11. The device according to claim 10, wherein the main objective is placed axially moveable in relation to the ophthalmoscope lens in longitudinal direction to the stereoscopic beam.

12. The device according to claim 1, wherein upstream of the optical deflection means, an interchangeable Galilean optic
is placed in longitudinal direction to the observation beam path and the illumination beam path, respectively.

13. The device according to claim 1, wherein the ophthalmoscope comprises the following components:
at least one illumination means which generates the illumination beam and one imaging optic which images the illumination beam via an intermediate image plane on the posterior segment of the eyeball,
at least one observation means and one imaging optic which is allocatable to the observation means and which images the observation beam generated by the reflection of the illumination beam at the posterior segment of the eyeball via the intermediate image plane into the observation means,
a split diaphragm system placed in the illumination beam and in the observation beam, the split diaphragm system having at least one split diaphragm which can be placed in the illumination beam and the observation beam, respectively, which oscillate synchronously relative to the illumination beam and the observation beam, with the intermediate image plane being infinitely imageable via the main objective, wherein the infinitely imaged intermediate image plane is imageable in an imaging plane of the observation beam, in which the imaging plane the observation means is provided, and
wherein the main objective is provided in the beam path of the observation beam downstream of the intermediate image plane and is passed through by the illumination beam as well as by the observation beam.

14. The device according to claim 10, wherein the ophthalmoscope lens, which images the posterior segment of the eyeball in the intermediate plane and the illumination beam on the posterior segment of the eyeball, is provided in the beam path in longitudinal direction to the illumination beam and the observation beam between the patient's eye and the intermediate image plane.

15. The device according to claim 1, wherein the main objective is at least one achromat.

16. The device according to claim 13, wherein an optic unit, which images the infinitely imaged intermediate plane in the imaging plane on the observation means, is provided in longitudinal direction to the observation beam.

17. The device according to claim 13, wherein an optic unit, which images the infinitely imaged intermediate image plane on a homogeneously lit area inside the imaging plane, is provided in longitudinal direction to the illumination beam.

18. The device according to claim 13, wherein the optical units in longitudinal direction to the observation beams and the illumination beams are combinable with a filter unit.

19. An ophthalmoscope for examining the posterior segment of a patient's eye comprising:
at least one illumination means, which generates at least one illumination beam, and one imaging optic, which is allocatable to the illumination means and which images the illumination beam via an intermediate image plane on the posterior segment of the patient's eye,
at least one observation means and one imaging optic which is allocatable to the observation means and which images an observation beam generated by reflection of the illumination beam on the posterior segment of the eye via the intermediate image plane in the observation means, as well as
a split diaphragm system placed in the illumination beam path and the observation beam path, having at least one split diaphragm which can be placed in the illumination beam and the observation beam, respectively, and oscillates synchronously relative to the illumination beam and observation beam, with the intermediate image plane being infinitely imageable via at least one optical unit, in such a manner that the infinitely imaged intermediate image plane is imageable in an imaging plane of the observation beam, in which the observation means is provided and the optical unit is provided in the observation beam path downstream of the
intermediate image plane and is passed through by both the illumination beam and the observation beam, wherein in the region of the infinitely imaged intermediate image plane, an optical deflection element is provided via which an additional beam path can be coupled in in longitudinal direction to the illumination beam and/or observation beam, and wherein the additional beam path is a projection beam path in longitudinal direction to which an objective is placed in whose focal point a display is placed which is infinitely imaged by the objective forming a parallel beam path which can be coupled in by the optical deflection element in longitudinal direction to the illumination beam and/or the observation beam.

20. The ophthalmoscope according to claim 19, wherein the additional beam path is focusable into the intermediate image plane via the optical unit.

21. The ophthalmoscope according to claim 19, wherein the display is a miniaturized LCD display.

22. The ophthalmoscope according to claim 21, wherein the LCD display has 1024×768 separately activatable, self-illuminating pixels.

23. The ophthalmoscope according to claim 19, wherein with the aid of a suited eye-tracking method the defect regions can be depicted in real time on the screen and can be documented.

24. Use of the ophthalmoscope according to claim 19 for microperimetric examination of the patient's eye by stimulating a predefined point on the fundus oculi of the patient's eye by means of pixel activation on the LCD display and projection of the pixel image on the fundus oculi.

* * * * *